United States Patent [19]

Müller et al.

[11] Patent Number: 5,183,932
[45] Date of Patent: Feb. 2, 1993

[54] HERBICIDAL SUBSTITUTED 4-AMINO-5-ALKYLTHIO-1,2,4-TRIAZOL-3-ONES

[75] Inventors: Klaus-Helmut Müller, Duesseldorf; Joachim Kluth, Langenfeld; Klaus König, Odenthal; Karl-Rudolf Gassen, Odenthal; Kurt Findeisen, Odenthal; Markus Lindig, Hilden; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 654,124

[22] Filed: Feb. 12, 1991

Related U.S. Application Data

[62] Division of Ser. No. 504,463, Apr. 4, 1990, Pat. No. 5,021,080.

[30] Foreign Application Priority Data

Apr. 7, 1989 [DE] Fed. Rep. of Germany ....... 3911219
Oct. 10, 1989 [DE] Fed. Rep. of Germany ....... 3933750

[51] Int. Cl.$^5$ .................. C07C 265/10; C07C 211/16
[52] U.S. Cl. ................................. 560/330; 564/191; 564/1; 562/867; 562/849; 562/505; 560/123
[58] Field of Search .................. 562/867, 849, 505; 560/123, 330; 564/1, 191

[56] References Cited

U.S. PATENT DOCUMENTS 2,441,128 5/1948 Barrick et al. ...................... 558/433
5,025,030 6/1991 Lantzsch et al. .................. 548/101

OTHER PUBLICATIONS

W. J. Middleton, *J. Org. Chem.*, "Perfluorovinyl Isocynates," 38(22), pp. 3924–3928 (1973).
D. Grahm, *J. Ors. Chem.* 31, 955 (1966), pp. 955–956.
Coffman et al., *J. American Chem, Soc.* 71, (1949), pp. 490–496.
L. Bretherick, *Handbook of Reactive Chemical Harrods*, Third Edition, Bufferworth, London 1985.
"Tetrafluorethylen (Perfluorethylen)", definition, German Dictionary.

Primary Examiner—Richard L. Raymond
Assistant Examiner—Mark W. Russell
Attorney, Agent, or Firm—Sprung Horn Kramer & Woods

[57] ABSTRACT

Herbicidal substituted 4-amino-5-alkylthio-1,2,4-triazol-3-ones of the formula $$R^2-NH-\overset{O}{\underset{\|}{C}}-N\underset{N=}{\overset{\overset{O}{\|}}{\underset{|}{N}}}\overset{NH_2}{\underset{S-R^1}{N}}\quad (I)$$

in which
R$^1$ represents in each case straight-chain or branched alkyl, alkenyl or alkinyl, each of which has up to 4 carbon atoms, and
R$^2$ represents sec-butyl, tert.-butyl or optionally substituted C$_5$–C$_{10}$-alkyl, alkenyl or alkinyl, or piperidyl- or morpholinyl-alkyl, optionally substituted C$_3$, C$_4$, C$_5$ and C$_7$-cycloalkyl, substituted cyclohexyl, or optionally substituted benzyl, phenethyl, naphthylmethyl or naphthylethyl.

3 Claims, No Drawings

HERBICIDAL SUBSTITUTED 4-AMINO-5-ALKYLTHIO-1,2,4-TRIAZOL-3-ONES

This is a division, of application Ser. No. 504,463, filed Apr. 4, 1990 now U.S. Pat. No. 5,021,080.

The invention relates to new substituted 4-amino-5-alkylthio-1,2,4-triazol-3-ones, to several processes and new intermediates for their preparation, and to their use as herbicides.

It is known that certain 4-amino-5-alkylthio-1,2,4-triazol-3-ones, such as, for example, 4-amino-5-methylthio-2-cyclohexylaminocarbonyl-2,4-dihydro-3H-1,2,4-triazol-3-one, 4-amino-5-methylthio-2-isopropylaminocarbonyl-2,4-dihydro-3H-1,2,4-triazol-3-one and 4-amino-5-methylthio-2-butylaminocarbonyl-2,4-dihydro-3H-1,2,4-triazol-3-one, are herbicidally active (cf. Japanese Patent 52-125,168). However, the action of these known compounds is not satisfactory in all respects.

The new substituted 4-amino-5-alkylthio-1,2,4-triazol-3-ones of the general formula (I)

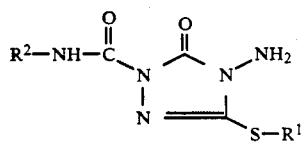

in which
$R^1$ represents in each case straight-chain or branched alkyl, alkenyl or alkinyl, each of which has up to 4 carbon atoms, and
$R^2$ represents sec.-butyl, tert.-butyl, in each case straight-chain or branched $C_5$–$C_{10}$-alkyl, $C_5$–$C_{10}$-alkenyl or $C_5$–$C_{10}$-alkinyl, or represents straight-chain or branched alkyl, alkenyl or alkinyl, each of which has up to 10 carbon atoms and each of which is substituted by halogen, cyano, $C_3$–$C_6$-cycloalkyl, aryloxy having 6 to 10 carbon atoms (in particular phenyl or naphthyl) or $C_1$–$C_6$-alkoxy, or represents $C_1$–$C_6$-alkyl which is in each case substituted by piperidyl or morpholinyl, or represents cyclopropyl, cyclobutyl, cyclopentyl or cycloheptyl, each of which is optionally substituted by halogen, aryl having 6 to 10 carbon atoms (in particular phenyl or naphthyl), $C_1$–$C_6$-alkyl or $C_1$–$C_4$-halogenoalkyl, or represents cyclohexyl which is substituted by halogen, $C_1$–$C_6$-alkyl, $C_2$–$C_4$-alkenyl or $C_1$–$C_4$-halogenoalkyl, or represents phenyl-$C_1$–$C_2$-alkyl or naphthyl-$C_1$–$C_2$-alkyl, each of which is optionally substituted in the aromatic component by halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_4$-alkylsulphinyl, $C_1$–$C_4$-alkylsulphonyl, phenoxy and/or phenyl,
have now been found.

The individual carbon chains in, for example, alkyl, halogenoalkyl or alkenyl, are in each case straight-chain or branched.

Furthermore, it has been found that the new substituted 4-amino-5-alkylthio-1,2,4-triazol-3-ones of the general formula (I)

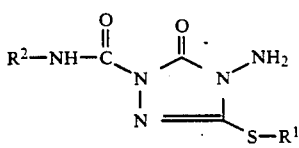

in which
$R^1$ represents in each case straight-chain or branched alkyl, alkenyl or alkinyl, each of which has up to 4 carbon atoms, and
$R^2$ represents sec.-butyl, tert.-butyl, in each case straight-chain or branched $C_5$–$C_{10}$-alkyl, $C_5$–$C_{10}$-alkenyl or $C_5$–$C_{10}$-alkinyl, or represents straight-chain or branched alkyl, alkenyl or alkinyl, each of which has up to 10 carbon atoms and each of which is substituted by halogen, cyano, $C_3$–$C_6$-cycloalkyl, aryloxy having 6 to 10 carbon atoms (in particular phenyl or naphthyl) or $C_1$–$C_6$-alkoxy, or represents $C_1$–$C_6$-alkyl which is in each case substituted by piperidyl or morpholinyl, or represents cyclopropyl, cyclobutyl, cyclopentyl or cycloheptyl, each of which is optionally substituted by halogen, aryl having 6 to 10 carbon atoms (in particular phenyl or naphthyl), $C_1$–$C_6$-alkyl or $C_1$–$C_4$-halogenoalkyl, or represents cyclohexyl which is substituted by halogen, $C_1$–$C_6$-alkyl, $C_2$–$C_4$-alkenyl or $C_1$–$C_4$-halogenoalkyl, or represents phenyl-$C_1$–$C_2$-alkyl or naphthyl-$C_1$–$C_2$-alkyl, each of which is optionally substituted in the aromatic component by halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_4$-alkylsulphinyl, $C_1$–$C_4$-alkylsulphonyl, phenoxy and/or phenyl,
are obtained when
(a) hydrazones of the general formula (II)

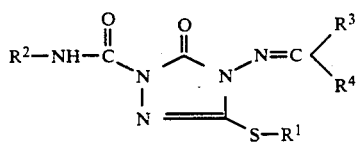

in which
$R^1$ and $R^2$ are as defined above and
$R^3$ and $R^4$ independently of one another each represent hydrogen, $C_1$–$C_6$-alkyl, phenyl-$C_1$–$C_4$-alkyl or phenyl,
are reacted with an acid, if appropriate in the presence of a diluent, or when
b) triazolones of the general formula (III)

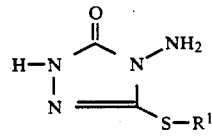

in which
$R^1$ is as defined above,
are reacted with isocyanates of the general formula (IV)

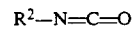

$$R^2-N=C=O \qquad (IV)$$

in which $R^2$ is as defined above, if appropriate in the presence of a diluent and if appropriate in the presence of a reaction auxiliary, or when c) oxycarbonyltriazolones of the general formula (V)

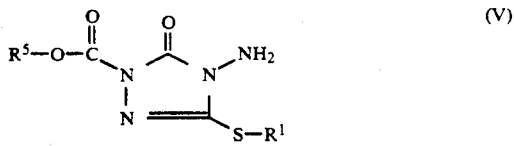

in which $R^1$ is as defined above and $R^5$ represents $C_1-C_6$-alkyl, phenyl or phenyl-$C_1-C_4$-alkyl, are reacted with amines of the general formula (VI)

$R^2$—NH$_2$ (VI)

in which $R^2$ is as defined above, if appropriate in the presence of a diluent and if appropriate in the presence of a reaction auxiliary.

Finally, it has been found that the new substituted 4-amino-5-alkylthio-1,2,4-triazol-3-ones of the general formula (I) have interesting herbicidal properties.

Surprisingly, the substituted 4-amino-5-alkylthio-1,2,4-triazol-3-ones of the general formula (I) according to the invention show a considerably more powerful herbicidal action against problem weeds than the known, herbicidally active compounds 4-amino-5-methylthio-2-cyclohexylaminocarbonyl-2,4-dihydro-3H-1,2,4-triazol-3-one, 4-amino-5-methylthio-2-isopropylaminocarbonyl-2,4-dihydro-3H-1,2,4-triazol-3-one and 4-amino-5-methylthio-2-butylaminocarbonyl-2,4-dihydro-3H-1,2,4-triazol-3-one, which are substances of a similar structure.

The invention preferably relates to compounds of the formula (I) in which $R^1$ represents methyl, ethyl, propyl, isopropyl, butyl, isobutyl, sec.-butyl, tert.-butyl, allyl, crotonyl or propargyl and $R^2$ represents sec.-butyl, tert.-butyl, in each case straight-chain or branched pentyl, hexyl, heptyl, octyl, pentenyl, hexenyl, heptenyl, octenyl, pentinyl, hexinyl, heptinyl or octinyl, or represents methyl, ethyl, propyl, isopropyl, butyl, isobutyl, sec.-butyl, tert.-butyl, pentyl, isopentyl, sec.-pentyl, tert.-pentyl, allyl, crotonyl or propargyl, each of which is substituted by fluorine, chlorine, bromine, cyano, cyclopropyl, cyclobutyl, cyclopentyl, cyclohexyl, phenoxy, methoxy, ethoxy, propoxy, isopropoxy, butoxy, isobutoxy, sec.-butoxy or tert.-butoxy, or $R^2$ furthermore represents methyl, ethyl, n- or isopropyl, each of which is substituted by piperidinyl or morpholinyl, or represents cyclopropyl, cyclobutyl or cyclopentyl, each of which is optionally substituted by fluorine, chlorine, bromine, methyl, trifluoromethyl, ethyl, propyl, isopropyl, butyl, isobutyl, sec.-butyl or tert.-butyl, or represents cyclohexyl which is substituted by fluorine, chlorine, methyl, trifluoromethyl, ethyl, propyl, isopropyl, butyl, isobutyl, sec.-butyl, tert.-butyl or propargyl, $R^2$ furthermore represents benzyl or phenylethyl, each of which is optionally substituted in the aromatic component by fluorine, chlorine, bromine, methyl, ethyl, propyl, isopropyl, trifluoromethyl, methoxy, ethoxy, difluoromethoxy, trifluoromethoxy, methylthio, methylsulphinyl, methylsulphonyl, phenoxy and/or phenyl.

In particular, the invention relates to compounds of the formula (I) in which $R^1$ represents methyl, ethyl, n-propyl, isopropyl or allyl, $R^2$ represents sec.-butyl, tert.-butyl, in each case straight-chain or branched pentyl, hexyl, heptyl, pentenyl, hexenyl, heptenyl, pentinyl, hexinyl or heptinyl, or represents methyl, ethyl, propyl, isopropyl, butyl, isobutyl, sec.-butyl or tert.-butyl, each of which is substituted by fluorine, chlorine, methoxy, phenoxy or cyano, or represents cyclopropyl, cyclobutyl or cyclopentyl, each of which is optionally substituted by fluorine, chlorine, methyl, trifluoromethyl, ethyl, propyl, isopropyl, butyl, isobutyl, sec.-butyl or tert.-butyl, or represents cyclohexyl which is substituted by chlorine, methyl, trifluoromethyl, ethyl, propyl, isopropyl, butyl, isobutyl, sec.-butyl or tert.-butyl, or represents (R/S)-, (R)- or (S)-1-phenylethyl which is optionally substituted in the aromatic component by fluorine, chlorine, bromine, methyl, ethyl, methoxy, ethoxy, ethoxy and/or phenyl.

If, for example, 4-isopropylidenimino-5-ethylthio-2-tert.-butylaminocarbonyl-2,4-dihydro-3H-1,2,4-triazol-3-one is used as the starting compound, the course of the reaction of process (a) according to the invention may be represented by the following equation:

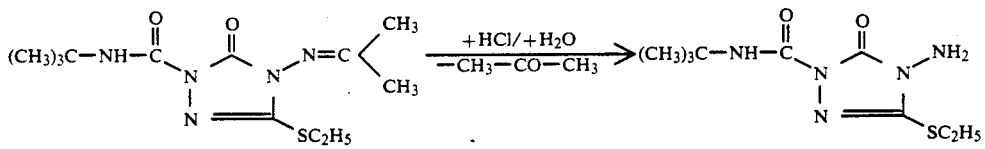

If, for example, 4-amino-5-ethylthio-2,4-dihydro-3H-1,2,4-triazol-3-one and tert.-butyl isocyanate are used as the starting substances, the course of the reaction of process (b) according to the invention may be represented by the following equation:

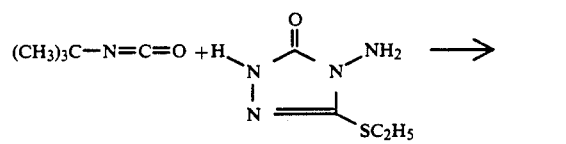

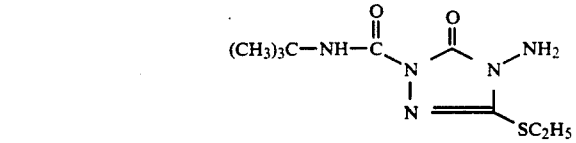

If, for example, 4-amino-5-ethylthio-2-methoxycarbonyl-2,4-dihydro-3H-1,2,4-triazol-3-one and 2-cyanoethylamine are used as the starting substances, the course of the reaction of process (c) according to the invention may be represented by the following equation:

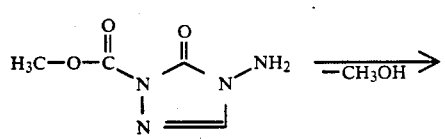

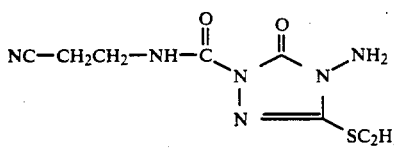

Formula (II) provides a general definition of the hydrazones to be used as starting substances in process (a) according to the invention for the preparation of compounds of the formula (I).

In formula (II), $R^1$ and $R^2$ preferably, or in particular, have those meanings which have already been mentioned above in connection with the description of the compounds of the formula (I) according to the invention as being preferred, or particularly preferred, for $R^1$ and $R^2$;

$R^3$ and $R^4$, in each case independently of one another, preferably represent hydrogen, straight-chain or branched alkyl having 1 to 4 carbon atoms, or phenyl or benzyl, in particular hydrogen, methyl, ethyl, phenyl or benzyl.

The hydrazones of the formula (II) were hitherto unknown. They are likewise the subject-matter of the present invention. However, they are obtained in analogy to known processes (cf., for example, Acta Pol. Pharm. 38, 153–162 [1981] or C.A. 95: 203841j), for example when triazolones of the formula (III)

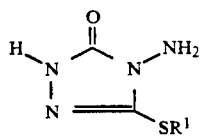

in which
$R^1$ is as defined above,
are reacted with aldehyde or ketones of the formula (VII)

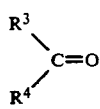 (VII)

in which
$R^3$ and $R^4$ are as defined above,
if appropriate in the presence of a diluent, such as, for example, dichloromethane or toluene, and, if appropriate, in the presence of a catalyst, such as, for example, p-toluene sulphonic acid, at temperatures between 40° C. and 120° C., and the resulting triazolone hydrazones of the formula (VIII)

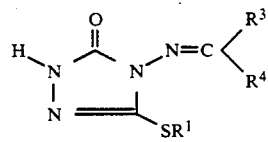

in which
$R^1$, $R^3$ and $R^4$ are as defined above,
are either reacted, in a subsequent second step, with isocyanates of the formula (IV),

 (IV)

in which
$R^2$ is as defined above,
if appropriate in the presence of a diluent, such as, for example, dichloromethane or dioxane, and, if appropriate, in the presence of a reaction auxiliary, such as, for example, triethylamine, at temperatures between 20° C. and 150° C.; or, alternatively, in a subsequent second step, with chloroformic acid esters of the formula (IX),

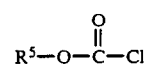 (IX)

in which
$R^5$ is as defined above,
if appropriate in the presence of a diluent, such as, for example, tetrahydrofuran, and, if appropriate, in the presence of a reaction auxiliary, such as, for example, sodium hydride or potassium tert.-butoxide, at temperatures between −20° C. and +40° C., and the resulting triazolones of the formula (X)

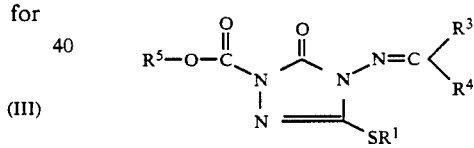

in which
$R^1$, $R^3$, $R^4$ and $R^5$ are as defined above,
are reacted, in a subsequent third step, with amines of the formula (VI)

 (VI)

in which
$R^2$ is as defined above,
is appropriate in the presence of a diluent, such as, for example, tetrahydrofuran or dioxane, and, if appropriate, in the presence of a base, such as, for example, sodium hydroxide or potassium hydroxide, at temperatures between 20° C. and 100° C.

In doing this, it is also possible and may be advantageous to react the triazolone hydrazones of the formula (VIII) with chloroformic acid esters of the formula (IX) and to subsequently react the resulting triazolones (X) with amines of the formula (VI) in a so-called one-pot process.

The triazolones of the formula (III) are known or can be obtained in analogy to known processes (cf., for example, Japanese Patent 52-125,168).

The aldehydes or ketones of the formula (VII), the isocyanates of the formula (IV), the chloroformic acid esters of the formula (IX) and the amines of the formula (VI) are mostly known chemicals for organic synthesis.

The trizolone hydrazones of the formula (VIII) and the triazolones of the formula (X) were hitherto unknown from the literature and form the subject-matter of the present patent application.

In the formulae (VIII) and (X), $R^1$, $R^3$ and $R^4$ preferably, or in particular, have the meaning which has been mentioned above in connection with the description of the compounds of the formulae (I) and (II) according to the invention as being preferred, or particularly preferred, for $R^1$, $R^3$ and $R^4$. $R^5$ preferably represents methyl, ethyl, propyl, isopropyl, butyl, isobutyl, secbutyl, tert-butyl, phenyl or benzyl.

Formula (III) provides a general definition of the triazolones to be used as starting substances in process (b) according to the invention for the preparation of compounds of the formula (I).

In formula (III), $R^1$ preferably, or in particular, has the meaning which has already been mentioned above in connection with the description of the compounds of the formula (I) according to the invention as being preferred, or particularly preferred, for $R^1$.

The triazolones of the formula (III) are known or can be obtained in analogy to known processes (cf., for example, Japanese Patent 52-125,168).

Formula (IV) provides a general definition of the isocyanates furthermore required as the starting substances for carrying out process (b) according to the invention. In this formula (IV), $R^2$ preferably represents those radicals which have already been mentioned in connection with the description of the substances of the formula (I) according to the invention as being preferred for $R^2$.

The isocyanates of the formula (IV) are mostly known chemicals for organic synthesis.

Formula (V) provides a general definition of the oxycarbonyltriazolones to be used as substances in process (c) according to the invention for the preparation of compounds of the formula (I).

In formula (V), $R^1$ and $R^5$ preferably, or in particular, have those meanings which have already been mentioned above in connection with the description of the compounds of the formulae (I) and (VIII) according to the invention as being preferred, or particularly preferred, for $R^1$, and as preferred for $R^5$.

The oxycarbonyltriazolones of the formula (V) were hitherto unknown from the literature and form the subject-matter of the present patent application.

The new compounds of the formula (V) are obtained when triazolones of the formula (III)

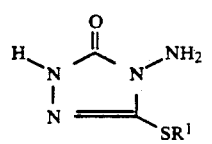

in which
$R^1$ is as defined above,
are reacted with chloroformic acid esters of the formula (IX)

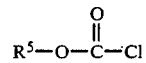

in which
$R^5$ has the abovementioned meaning,
if appropriate in the presence of a diluent, such as, for example, tetrahydrofuran, and, if appropriate, in the presence of a reaction auxiliary, such as, for example, potassium tert-butoxide or sodium hydride, at temperatures between −20° C. and +100° C.

Other new compounds which form the subject-matter of the present invention are 2-chloro-1-methyl-2,3,3-trifluoro-cyclobut-1-yl isocyanate of the formula (IVa),

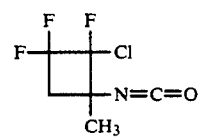

and 2-chloro-1-methyl-2,3,3-trifluoro-cyclobut-1-ylamine, of the formula (VIa)

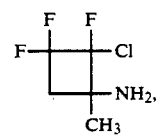

which can be employed as intermediates for the preparation of corresponding compounds of the formula (I).

The new compound of the formula (IVa) is obtained when 2-chloro-1-methyl-2,3,3-trifluoro-cyclobutane-1-carboxylic acid chloride, of the formula (X),

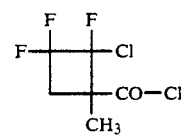

is reacted with trimethylsilyl azide, preferably in the presence of an inert diluent, such as, for example, toluene, at temperatures between 60° C. and 80° C., and the product is isolated by distillation in vacuo.

The compound of the formula (IVa) can also be prepared from the compound of the formula (VIa) by customary methods, for example by phosgenation.

The new compound of the formula (X) which also forms subject matter of the present application is obtained when 2-chloro-1-methyl-2,3,3-trifluoro-cyclobutane-2-carboxylic acid, of the formula (XI),

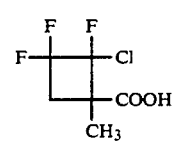

is reacted with an acid chloride which is suitable for chlorination, such as, for example, thionyl chloride or phthalic acid dichloride, at temperatures between 0° C. and 100° C., and the product is isolated by distillation in vacuo.

The new compound of the formula (XI) which also forms subject matter of the present application is obtained when 2-chloro-1-methyl-2,3,3-trifluoro-cyclobutane-1-carboxylic acid esters of the formula (XII)

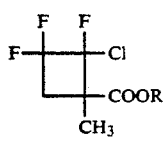
(XII)

in which
R represents lower alkyl, preferably $C_1$-$C_4$-alkyl, especially methyl or ethyl, are reacted with an aqueous solution of an alkali metal hydroxide, such as, for example, with aqueous sodium hydroxide solution, at temperatures between 50° C. and 100° C., the mixture is then acidified with a strong acid, such as, for example, hydrochloric acid, and then extracted with an organic solvent which is virtually immiscible with water, such as, for example, methylene chloride, and the product is isolated from the organic phase by distillation in vacuo.

The new compounds of the formula (XII) which also form subject matter of the present application are obtained when methacrylic acid esters of the formula (XIII)

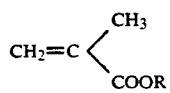
(XIII)

in which
R represents lower alkyl, preferably $C_1$-$C_4$-alkyl, especially methyl or ethyl, are heated together with chlorotrifluoroethene in an autoclave, preferably in the presence of a stabilizer, such as, for example, hydroquinone, at temperatures between 50° C. and 150° C., and the product is subsequently isolated by distillation in vacuo.

The new starting compound of the formula (VIa)

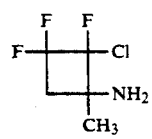
(VIa)

is obtained when 2-chloro-1-methyl-2,3,3-trifluoro-cyclobutane-1-carboxamide of the formula (XIV),

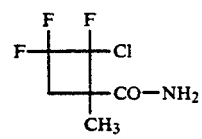
(XIV)

is reacted with sodium hypochlorite in water at temperatures between 0° C. and 20° C., the mixture is subsequently treated with a strong base, such as, for example, sodium hydroxide, and heated to a temperature of between 60° C. and 100° C., and, finally, the mixture is preliminarily purified by steam distillation. The oily steam distillation product can be purified further by distillation in vacuo.

2-Chloro-1-methyl-2,3,3-trifluoro-cyclobutane-1-carboxamide of the formula (XIV) and required as intermediate, was hitherto unknown from the literature and forms the subject-matter of the present invention.

The new compound of the formula (XIV) is obtained when 2-chloro-1-methyl-2,3,3-trifluoro-cyclobutane-1-carboxylic acid esters of the formula (XII)

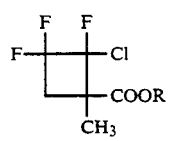
(XII)

are reacted with ammonia in an autoclave at temperatures between 20° C. and 80° C., if appropriate in the presence of a diluent, such as, for example, methanol, and, if appropriate, in the presence of a reaction auxiliary, such as, for example, sodium methoxide, the mixture is subsequently acidified with ice-cooling and extracted with an organic solvent which is virtually immiscible with water, such as, for example, methylene chloride, and the product is isolated from the organic phase by distillation in vacuo.

The new compounds of the formula (IVa), (VIa), (XIV), (X), (XI) and (XII) are all embraced by the generic formula (XV)

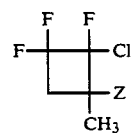
(XV)

in which
Z represents N=C=O, $NH_2$, CO—$NH_2$, CO—Cl, COOH or COOR, where R is lower alkyl.

Acids which are suitable for carrying out process (a) according to the invention are all inorganic and organic acids which can customarily be used for hydrazone cleavages. Inorganic mineral acids, such as hydrochloric acid, sulphuric acid or phosphoric acid, are preferably used.

Suitable diluents for carrying out process (a) according to the invention are all customary organic or inorganic solvents. Diluents which are preferably used are polar, water-miscible, organic solvents, in particular alcohols, such as methanol, ethanol, propanol or butanol, their mixtures with water, or pure water.

When carrying out process (a) according to the invention, the reaction temperatures can be varied within a substantial range. In general, the process is carried out at temperatures between 20° C. and 150° C., preferably at temperatures between 50° C. and 120° C.

Process (a) according to the invention is customarily carried out under atmospheric pressure or under reduced pressure. If the process is carried out under reduced pressure, the pressure ranges which are suitable are those between 20 and 400 mbar, preferably between 100 and 200 mbar.

For carrying out process (a) according to the invention, 0.01 to 50 moles, preferably 0.01 to 20 moles, of acid are generally employed per mole of hydrazone of the formula (II). For this purpose, the hydrazone of the formula (II) is dissolved in a suitable amount of diluent, the necessary amount of acid is then added, and the mixture is slowly concentrated under reduced pressure in the course of several hours.

In a particular embodiment, it is also possible to carry out process (a) according to the invention and to prepare the precursors of the formula (II) required for this purpose, in one reaction step, in a so-called one-pot process.

In doing this, one possibility is to choose the triazolones of the formula (X) as the starting compounds and to react them in succession in a one-pot process with amines of the formula (VI) and then with acid, according to process (a) according to the invention, or to choose the triazolone hydrazones of the formula (VIII) as the starting compounds and to react these in succession in a one-pot process with chloroformic acid esters of the formula (IX), then with amines of the formula (VI) and then with acid, according to process (a) according to the invention, or to choose the triazolones of the formula (III) as the starting compounds and to react these in succession in a one-pot process with aldehydes or ketones of the formula (VII), then with isocyanates of the formula (IV) and subsequently with acid, according to process (a) according to the invention.

Diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or esters, such as ethyl acetate.

If appropriate, process (b) according to the invention is carried out in the presence of a suitable reaction auxiliary. Suitable reaction auxiliaries are all customary inorganic or organic bases. These include, for example, tertiary amines, such as triethyl amine, N,N-dimethylaniline, N,N-diethylbenzylamine, N,N-dimethylcyclohexylamine or dibutyltin dilaurate, pyridine, N,N-dimethylaminopyridine, diazabicyclooctane (DABCO), diazabicylononene (DBN) or diazabicyloundecene (DBU).

When carrying out process (b) according to the invention, the reaction temperatures can be varied within a substantial range. In general, the process is carried out at temperatures between 0° C. and 150° C., preferably at temperatures between 20° C. and 100° C.

For carrying out process (b) according to the invention, 1.0 to 2.0 moles, preferably 1.0 to 1.5 moles, of isocyanate of the formula (IV) and, if appropriate, 0.001 to 2.0 moles, preferably 0.001 to 1.0 mole, of reaction auxiliary are generally employed per mole of triazolone of the formula (III).

The reaction is carried out and the reaction products are worked up and isolated by generally customary methods.

Suitable diluents for carrying out process (c) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or esters, such as ethyl acetate, or sulphoxides, such as dimethyl sulphoxide.

If appropriate, process (c) according to the invention can be carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethyl amine, N,N-dimethylaniline, pyridine, N,N-dimethylaminopyridine, diazabicyclooctane (DABCO), diazabicylononene (DBN) or diazabicyloundecene (DBU).

When carrying out process (c) according to the invention, the reaction temperatures can be varied within a substantial range. In general, the process is carried out at temperatures between 0° C. and 120° C., preferably at temperatures between 20° C. and 50° C.

For carrying out process (c) according to the invention, 1.0 to 5.0 moles, preferably 1.0 to 2.5 moles, of amine of the formula (VI) and, if appropriate, 1.0 to 2.5 moles, preferably 1.0 to 1.2 moles, of reaction auxiliary are generally employed per mole of oxycarbonyltriazolone of the formula (V).

The reaction is carried out and the reaction products are worked and isolated by generally customary methods.

In a particular embodiment, it is also possible to carry out process (c) according to the invention and to prepare the precursors of the foumula (V) required for this purpose, in one reaction step, in a so-called one-pot process.

This process uses triazolones of the formula (III) as starting materials, which are reacted in succession in a one-pot process, initially with chloroformic acid esters of the formula (IX) and subsequently with amines of the formula (VI), according to process (c) according to the invention.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are also suitable for selectively combating monocotyledon and dicotyledon weeds in monocotyledon and dicotyledon cultures, both using the pre-emergence and the post-emergence methods.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatic and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); methyl-6,6-dimethyl-2,4-dioxo-3-[1-(2-propenyloxyamino)-butylidene]-cyclohexanecarboxylic acid (ALLOXYDIM); 2-chloro-4-ethylamino-6-isopropylamino1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); N-(butoxymethyl)-2-chloro-N-(2,6-diethylphenyl)-acetamide (BUTACHLOR); ethyl 2-{[(4-chloro-6-methoxy-2-pyrimidinyl)-aminocarbonyl]aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP); S-ethyl N,N-di-n-propyl-thiocarbamidate (EPTAME); 4-amino-6-t-butyl3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); [(4-amino-3,5- dichloro-6-fluoro-2-pyridinyl)-oxy]-acetic acid or its 1-methylheptyl ester (FLUROXYPYR); 5-(2-chloro-4-trifluoromethylphenoxy)-N-methylsulphonyl-2-nitrobenzamide (FOMESAFEN); 2-{4-[(3-chloro-5-(trifluoromethyl)-2-pyridinyl)-oxy]phenoxy}-propanoic acid or its ethyl ester (HALOXYFOP); 2-[5-methyl-5-(1-methylethyl)-4-oxo-2-imidazolin-2-yl]-3-quinolincarboxylic acid (IMAZAQUIN); 2-[4,5-dihydro-4-methyl-4-isopropyl-5-oxo-(1H)-imidazol-2-yl]-5-ethylpyridin-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); (2-ethoxy-1-methyl-2-oxo-ethyl) 5-[2-chloro-4-(trifluoromethyl)-phenoxy]-2-nitrobenzoate (LACTOFEN); (2-methyl-4-chlorophenoxy)acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}benzoic acid or its methyl ester (METSULFURON); S-ethyl N,N-hexamethylenethiocarbamate (MOLINATE); 4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); O-(6-chloro-3-phenylpyridazin-4-yl) S-octyl thiocarbonate (PYRIDATE); 2-[1-(ethoxyamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]carbonyl]-amino]-sulphonyl]-thiophene-2-carboxylate (THIAMETURON); S-[(4-chlorophenyl)-methyl]-N,N-diethylthiocarbamate (THIOBENCARB); N,N-diisopropyl S-(2,3,3-trichloroallyl) thiocarbamate (TRIALLATE); 2,6-dinitro-4-trifluoromethyl-N,N-dipropylaniline (TRIFLURALIN) and ethyl 2-[4-(6-chloro-2-quinoxalinyloxy)-phenoxy]propionate (QUIZALOFOP) are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

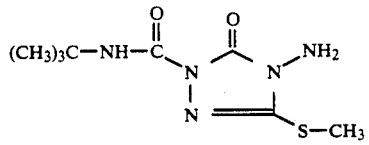

Process (a)-one-pot variant

A mixture of 7.3 g (0.05 mol) of 4-amino-5-methylthio-2,4-dihydro-3H-1,2,4-triazol-3-one, a spatula-tip full of p-toluenesulphonic acid and 100 ml of acetone is refluxed for 3 hours. After the mixture has been concentrated, the residue is taken up in 50 ml of acetonitrile, 5.5 g (0.055 mol) of tert-butyl isocyanate and 0.1 g of diazabicycloundecene (DBU) are added, and the mixture is then stirred for 12 hours at 20° C.

After the mixture has been reconcentrated, the residue which remains is taken up in 100 ml of ethanol/water (1:1), 5 ml of concentrated hydrochloric acid are added, and the mixture is then evaporated to dryness at 60° C. and under slightly subatmospheric pressure, within 3 hours. The residue is taken up in methylene chloride, the mixture is washed with water until neutral, dried using sodium sulphate and filtered. The solvent is removed from the filtrate by distillation in a water pump vacuum, and the product which remains in the residue is brought to crystallization by trituration with diethyl ether. This gives 6.0 g (49% of theory) of 4-amino-5-methylthio-2-tert-butylaminocarbonyl-2,4-dihydro-3H-1,2,4-triazol-3-one of melting point 134° C.

EXAMPLE 2

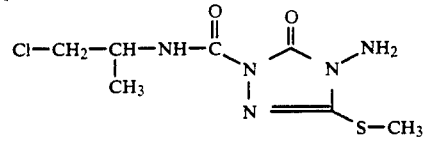

Process (b)

7.3 g (0.05 mol) of 4-amino-5-methylthio-2,4-dihydro-3H-1,2,4-triazol-3-one, are suspended in 100 ml of acetonitrile, 1 g of diazabicycloundecene (DBU) and 6.0 g (0.05 mol) of 2-chloro-1-methyl-ethyl isocyanate are added to the suspension with stirring, and the mixture is stirred for 12 hours at 20° C.

It is then concentrated, the residue is taken up in methylene chloride, the mixture is washed to neutrality, dried using sodium sulphate and filtered. The solvent is removed from the filtrate by distillation under a water pump vacuum, and the product which remains in the residue is brought to crystallization by trituration with diethyl ether. This gives 6.0 g (45% of theory) of 4-amino-5-methylthio-2-(2-chloro-1-methylethylaminocarbonyl)-2,4-dihydro-3H-1,2,4-triazol-3-one of melting point 136° C.

The compounds of the formula (I)

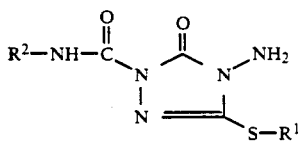

listed in Table 1 below can be prepared analogously to Examples 1 and 2 and following the general description of the preparation processes according to the invention.

TABLE 1

Examples of the compounds of the formula I

| Example No. | $R^1$ | $R^2$ | Melting point (°C.) |
|---|---|---|---|
| 3 | $CH_3$ | cyclopentyl-CH< | 110 |
| 4 | $CH_3$ | $-C(CH_3)_2C\equiv CH$ | 178 |
| 5 | $CH_3$ | $-C(CH_3)_2CH_2Cl$ | 125 |
| 6 | $CH_3$ | $-C(CH_3)_2(CH_2)_3CH_3$ | 95 |
| 7 | $CH_3$ | cyclopropyl | 124 |
| 8 | $CH_3$ | $-C(CH_3)_2CHCl_2$ | 172 |
| 9 | $CH_3$ | $-C(CH_2Cl)_2\text{-}CH_3$ | 141 |
| 10 | $CH_3$ | $-C(CH_3)_2CH_2F$ | 152 |
| 11 | $CH_3$ | $-C(CH_3)_2CN$ | 153 |
| 12 | $C_2H_5$ | $-C(CH_3)_3$ | |
| 13 | $C_2H_5$ | $-C(CH_3)_2CH_2Cl$ | 101 |
| 14 | $C_2H_5$ | $-C(CH_3)_2CH_2F$ | |
| 15 | $CH_3$ | $-CH_2-CF_3$ | |
| 16 | $CH_3$ | $-CH(CH_3)(CF_3)$ | |
| 17 | $CH_3$ | $-CH(C_2H_5)CH_2Cl$ | |
| 18 | $CH_3$ | $-CH(CH_3)CHCl(CH_3)$ | |
| 19 | $CH_3$ | $-CH(CH_2Cl)CH=CH_2$ | |
| 20 | $CH_3$ | $-CH(CH_3)-CH=CCl_2$ | |
| 21 | $CH_3$ | $-C(CH_3)(CH_2F)_2$ | |
| 22 | $CH_3$ | $-C(CH_3)_2CF_3$ | |
| 23 | $CH_3$ | $-CH(CH_3)C_3H_7$-n | |
| 24 | $CH_3$ | $-CH(CH_3)C_3H_7$-iso | |
| 25 | $CH_3$ | $-C(CH_3)(CN)C_3H_7$-iso | |
| 26 | $CH_3$ | $-CH(C_2H_5)_2$ | |
| 27 | $CH_3$ | $-C(CH_3)_2C_2H_5$ | |
| 28 | $CH_3$ | $-C(CH_3)_2CH=CCl_2$ | |
| 29 | $CH_3$ | $-C_6H_{13}$-n | |
| 30 | $CH_3$ | $-CH(CH_3)CH_2C_3H_7$-iso | |
| 31 | $CH_3$ | $-CH(CH_3)C_4H_9$-tert. | |
| 32 | $CH_3$ | $-C(CH_3)_2C_3H_7$-n | |
| 33 | $CH_3$ | $-C(CH_3)_2C_3H_7$-i | |
| 34 | $CH_3$ | $-C(CH_3)(C_2H_5)_2$ | |
| 35 | $CH_3$ | $-CH(CH_3)C_5H_{11}$-n | |
| 36 | $CH_3$ | $-CH(CH_3)C_4H_9$-n | |
| 37 | $CH_3$ | $-CH(CH_3)CH_2CH_2-C_3H_7$-iso | |
| 38 | $CH_3$ | $-CH(CH_3)CH_2-C_4H_9$-tert. | |
| 39 | $CH_3$ | $-C(CH_3)_2CH(CH_3)CH=CCl_2$ | |
| 40 | $CH_3$ | $-C(C_2H_5)_3$ | |
| 41 | $CH_3$ | $-CH(CH_3)C_6H_{13}$-n | |
| 42 | $CH_3$ | $-C(CH_3)_2-CH_2-C_4H_9$-t | |
| 43 | $CH_3$ | $-CH(CH_3)-(CH_2)_3-C_3H_7$-iso | |
| 44 | $CH_3$ | methyl-cyclopropyl | |
| 45 | $CH_3$ | methyl-(dichloromethyl)-cyclopropyl | |

TABLE 1-continued

Examples of the compounds of the formula I

| Example No. | R¹ | R² | Melting point (°C.) |
|---|---|---|---|
| 46 | CH₃ | 2,2-difluoro-3-methylcyclopropyl | |
| 47 | CH₃ | 2,2-dichloro-1,3,3-trimethylcyclopropyl | |
| 48 | CH₃ | 2-chloro-3,3-difluoro-2-methylcyclobutyl | 140 |
| 49 | CH₃ | 1-methylcyclopentyl | |
| 50 | CH₃ | 1-ethylcyclopentyl | |
| 51 | CH₃ | 1-methylcyclohexyl | |
| 52 | CH₃ | 1-ethylcyclohexyl | |
| 53 | CH₃ | 4-trifluoromethylcyclohexyl | |
| 54 | CH₃ | 4-ethylcyclohexyl | |
| 55 | CH₃ | 4-tert-butylcyclohexyl | |
| 56 | CH₃ | 1-cyclopropylethyl | |
| 57 | CH₃ | cyclohexylmethyl | |

TABLE 1-continued

Examples of the compounds of the formula I

| Example No. | R¹ | R² | Melting point (°C.) |
|---|---|---|---|
| 58 | $CH_3$ | CH(CH₃)—cyclohexyl | |
| 59 | $CH_3$ | CH(C₂H₅)—cyclohexyl | |
| 60 | $CH_3$ | CH₂—CH₂—cyclohexyl | |
| 61 | $CH_3$ | CH(CH₃)—CH₂—N(piperidine) | |
| 62 | $CH_3$ | CH(CH₃)—CH₂—N(morpholine) | |
| 63 | $CH_3$ | C(CH₃)₂—CH₂—N(morpholine) | |
| 64 | $CH_3$ | CH(CH₃)—CH₂—OCH₃ | |
| 65 | $CH_3$ | CH(CH₃)CH₂—O—C₆H₅ | |
| 66 | $CH_3$ | —CH(CH₃)—phenyl | |
| 67 | $CH_3$ | —CH(CH₃)—C₆H₄—F (4-) | 171- |
| 68 | $CH_3$ | —CH(CH₃)—C₆H₃—Cl₂ (2,4-) | 230 |
| 69 | $CH_3$ | —CH(CH₃)—C₆H₄—Cl (4-) | 147 |
| 70 | $CH_3$ | —CH(CH₃)—C₆H₃—Cl₂ (3,4-) | 132 |
| 71 | $CH_3$ | —CH(CH₃)—C₆H₄—C₂H₅ (4-) | 105 |

TABLE 1-continued

Examples of the compounds of the formula I

| Example No. | R¹ | R² | Melting point (°C.) |
|---|---|---|---|
| 72 | CH₃ | −CH(CH₃)−C₆H₄−Br (para) | 122 |
| 73 | CH₃ | −CH(CH₃)−C₆H₄−Br (meta) | 117 |
| 74 | CH₃ | −CH(CH₃)−(2,4,5-trimethylphenyl) | 127 |
| 75 | CH₃ | −CH(CH₃)−(4-biphenyl) | 167 |
| 76 | n-C₃H₇ | C(CH₃)₂CH₂Cl | |
| 77 | CH₃ | CH(CH₃)−C₂H₅ | 102 |
| 78 | CH₂CH=CH₂ | C(CH₃)₂CH₂Cl | 97 |
| 79 | CH₃ | −(CH₂)₂−O−C₂H₅ | 163 |

For example, the compound listed in Table 1 as Example 70 can be prepared as described below:

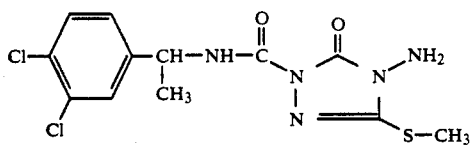

Process (c)

A mixture of 12.6 g (0.05 mol) of 4-amino-5-methylthio-2-phenoxycarbonyl-2,4-dihydro-3H-1,2,4-triazol-3-one, 9.5 g (0.05 mol) of 1-(3,4-dichlorophenyl)-ethylamine and 100 ml of tetrahydrofuran is stirred for 16 hours at 20° C. and subsequently concentrated. The residue is triturated with ethyl acetate, and the product obtained in the form of crystals is isolated by filtering off with suction.

This gives 2.9 g (16% of theory) of 4-amino-5-methylthio-2-(1-(3,4-dichloro-phenyl)-ethylaminocarbonyl)-2,4-dihydro-3H-1,2,4-triazol-3-one of melting point 132° C.

STARTING SUBSTANCES OF THE FORMULA (V)

Example (V-1)

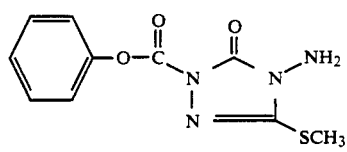

170 g (1.5 mol) of potassium tert.-butoxide is added in portions to a mixture of 201 g (1.40 mol) of 4-amino-5-methylthio-2,4-dihydro-3H-1,2,4-triazol-3-one and 1000 ml of tetrahydrofuran at 0° C. The reaction mixture is stirred for a further hour at 0° C. 214 g (1.4 mol) of phenyl chloroformate are subsequently added dropwise with stirring at 0° C. The reaction solution is stirred at 20° C. for a further 15 hours and concentrated on a rotary evaporator. 300 ml of water and 500 ml of methylene chloride are added to the residue. A colorless solid precipitates on the phase boundary and is isolated by filtration with suction.

This gives 218 g (63% of theory) of 4-amino-5-methylthio-2-phenoxycarbonyl-2,4-dihydro-3H-1,2,4-triazol-3-one of melting point 161° C.

The following is obtained analogously

Example (V-2)

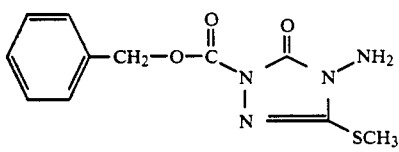

4-amino-5-methylthio-2-benzyloxycarbonyl-2,4-dihydro-3H1,2,4-triazol-3-one.

Example IVa

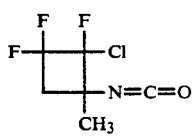

100 g (0.45 mol) of 1-methyl-2-chloro-2,3,3trifluorocyclobutanecarboxylic acid chloride are added dropwise to a solution of 61.3 g (0.53 mol) of trimethylsilyl azide in 250 ml of dry benzene. The mixture is heated to 75° C. and stirred until the evolution of gas has ceased. The solvent is subsequently distilled off, and the product which remains is fractionated.

This gives 77 g (86% of theory) of the above-shown product, boiling point: 75°-78° C./80 mm Hg.

Example X·

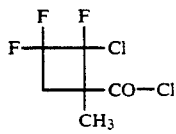

220 g (1.09 mol) of 1-methyl-2-chloro-2,3,3-trifluorocyclobutanecarboxylic acid are stirred overnight at room temperature with 250 g (1.23 mol) of phthalic acid dichloride. The acid chloride is subsequently distilled off.

This gives 238 g (99% of theory) of the above-shown product, boiling point: 54°-56° C./23 mm Hg.

Example XI

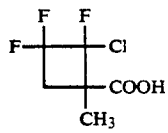

573 g (2.65 mol) of methyl 1-methyl-2-chloro-2,3,3-trifluorocyclobutanecarboxylate, 233 g (5.8 mol) of sodium hydroxide and 1000 ml of water are stirred for three hours at 80° C. The mixture is acidified using concentrated hydrochloric acid and extracted using dichloromethane, and the organic phases are dried and distilled. This gives 472 g (88% of theory) of the above-shown product, boiling point: 112°-116° C./16 mm Hg (60% of trans-isomer, 40% of cis-isomer).

Example XII-1

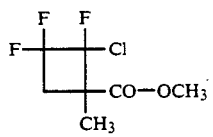

750 g (7.5 mol) of methyl methacrylate, 700 g (6.0 mol) of chlorotrifluoroethene and 3 g of hydroquinone are heated in a steel autoclave for 12 hours at 120° C. The product is fractionated directly.

This gives 780 g (60% of theory) of the above-shown product, boiling point: 57°-59° C./14 mm Hg.

Example XIV

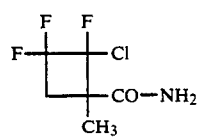

400 g (1.8 mol) of methyl 1-methyl-2-chloro-2,3,3-trifluorocyclobutanecarboxylate and 62 ml of 30% strength sodium methoxide solution are dissolved in 1500 ml of methanol, and 620 ml of liquid ammonia are added to the mixture in an autoclave. The mixture is stirred for 14 hours at 50° C., poured onto ice, slightly acidified using hydrochloric acid and extracted using dichloromethane. The combined organic phases are washed with dilute hydrogen carbonate solution, dried and concentrated. The amide is distilled.

This gives 254 g (68% of theory) of the above-shown product, boiling point: 138°-140° C./200 mg Hg.

Example VIa

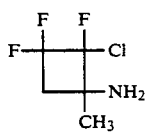

571 ml of 13% strength sodium hypochlorite solution (=1 mol NaOCl) are added dropwise at 10° C. to a suspension of 200 g (0.99 mol) of 1-methyl-2-chloro-2,3,3-trifluorocyclobutanecarboxamide in 1.2 l of water, during which process the amide slowly dissolves. Stirring is continued for 1 hour at 10° C., and 400 ml of 50% strength NaOH solution are added dropwise. The mixture is subsequently heated to 80° C., stirred at 80° C. for one hour and subjected to steam distillation. The amine is separated off and fractionated.

This gives 105 g (61% of theory) of the above-shown product, boiling point 54°-55° C./48 mm Hg.

Use Examples

In the use examples which follow, the compounds listed below were used as comparison substances:

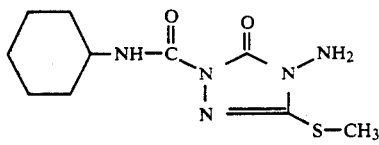

4-amino-5-methylthio-2-cyclohexylaminocarbonyl-2,4-dihydro-3H-1,2,4-triazol-3-one

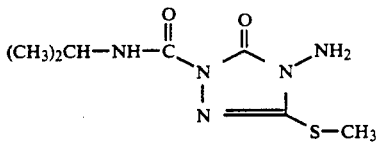

4-amino-5-methylthio-2-isopropylaminocarbonyl-2,4-dihydro-3H-1,2,4-triazol-3-one

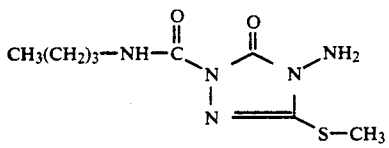

4-amino-5-methylthio-2-butylaminocarbonyl-2,4-dihydro-3H-1,2,4-triazol-3-one (all known from Japanese Patent 52-125,168).

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil, and, after 24 hours, watered with the preparation of active compound. In this context, it is expedient to keep constant the amount of water per unit area. The concentration of active compound in the preparation is of no importance, only the application rate of active compound per unit area being decisive. After three weeks, the degree of damage to the plants is rated in % damage in comparison to the development of the untreated control. The figures denote:

0% = no action (like untreated control)
100% = total destruction

A clearly superior effectiveness compared with the known compounds (A) and (C) is shown in this test, for example, by the compounds of Preparation Examples (1), (4), (5), (9) and (10).

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

A clearly superior effectiveness (combined with good selectivity towards crop plants) compared with the known compounds (A), (B) and (C) is shown in this test, for example, by the compounds of Preparation Examples (3), (4), (5), (6), (7), (10), (67), (71) and (73).

It is understood that the specification and examples are illustrative but not limitative of the present invention and that other embodiments with the spirit and scope of the invention will suggest themselves to those skilled in the art.

We claim:

1. A compound of the formula (XV)

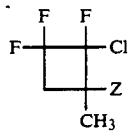

in which
Z represents N=C=O, or NH$_2$.

2. A compound according to claim 1, in which Z is NH$_2$.

3. A compound according to claim 1, in which Z is N=C=O.